(12) United States Patent
Stevens

(10) Patent No.: US 11,814,770 B2
(45) Date of Patent: Nov. 14, 2023

(54) UV-TREATMENT IN INDUSTRIAL LAUNDRY ON INTERMITTENT WASHING SYSTEMS

(71) Applicant: CHT Germany GmbH, Tübingen (DE)

(72) Inventor: Prince Charles Stevens, Altheim (DE)

(73) Assignee: CHT GERMANY GMBH

( * ) Notice: Subject to any disclaimer, the term of this patent is extended or adjusted under 35 U.S.C. 154(b) by 1055 days.

(21) Appl. No.: 16/606,365

(22) PCT Filed: Apr. 17, 2018

(86) PCT No.: PCT/EP2018/059707
§ 371 (c)(1),
(2) Date: Oct. 18, 2019

(87) PCT Pub. No.: WO2018/197253
PCT Pub. Date: Nov. 1, 2018

(65) Prior Publication Data
US 2023/0027554 A1    Jan. 26, 2023

(30) Foreign Application Priority Data

Apr. 25, 2017    (DE) .......................... 102017206924.4

(51) Int. Cl.
| | |
|---|---|
| *D06F 31/00* | (2006.01) |
| *A61L 2/10* | (2006.01) |
| *D06F 39/02* | (2006.01) |
| *D06F 39/00* | (2020.01) |
| *D06F 35/00* | (2006.01) |

(52) U.S. Cl.
CPC .............. *D06F 31/005* (2013.01); *A61L 2/10* (2013.01); *D06F 35/008* (2013.01); *D06F 39/022* (2013.01); *A61L 2202/11* (2013.01); *A61L 2202/17* (2013.01); *A61L 2202/26* (2013.01); *D06F 39/006* (2013.01)

(58) Field of Classification Search
CPC .... A61L 2/10; A61L 2202/11; A61L 2202/17; A61L 2202/26; D06F 31/005; D06F 35/008; D06F 39/022
See application file for complete search history.

(56) References Cited

U.S. PATENT DOCUMENTS

| | | |
|---|---|---|
| 2004/0033921 A1 | 2/2004 | Dasque et al. |
| 2016/0053425 A1 | 2/2016 | Wolff |

FOREIGN PATENT DOCUMENTS

| | | |
|---|---|---|
| DE | 4319177 A1 | 2/1994 |
| DE | 19954668 A1 | 5/2001 |
| DE | 102014213312 A1 | 1/2016 |
| DE | 102016105018 A1 | 9/2017 |
| EP | 1363987 B1 | 10/2005 |
| JP | 57-1497 A | 1/1982 |
| JP | 11-267692 A | 10/1999 |

(Continued)

OTHER PUBLICATIONS

International Search Report for International Application No. PCT/EP2018/059707 dated Jul. 16, 2018.

*Primary Examiner* — Sean E Conley
(74) *Attorney, Agent, or Firm* — Seth L. Hudson; Maynard Nexsen PC

(57) ABSTRACT

The present invention relates to a method for washing textiles in an intermittent washing system using UV radiation, to a device for carrying out the method, and to the use of UV radiation, in particular UV-C radiation, in methods for washing textiles in intermittent washing systems.

10 Claims, 1 Drawing Sheet

(56) References Cited

FOREIGN PATENT DOCUMENTS

| | | | |
|---|---|---|---|
| JP | 2004538112 | A | 12/2004 |
| JP | 2005319068 | A | 11/2005 |
| JP | 2006230957 | A | 9/2006 |
| JP | 2015112206 | A | 6/2015 |
| WO | 03/016608 | A1 | 2/2003 |
| WO | 2010/144744 | A2 | 12/2010 |
| WO | 2014/031478 | A1 | 2/2014 |
| WO | 2014/146165 | A1 | 9/2014 |

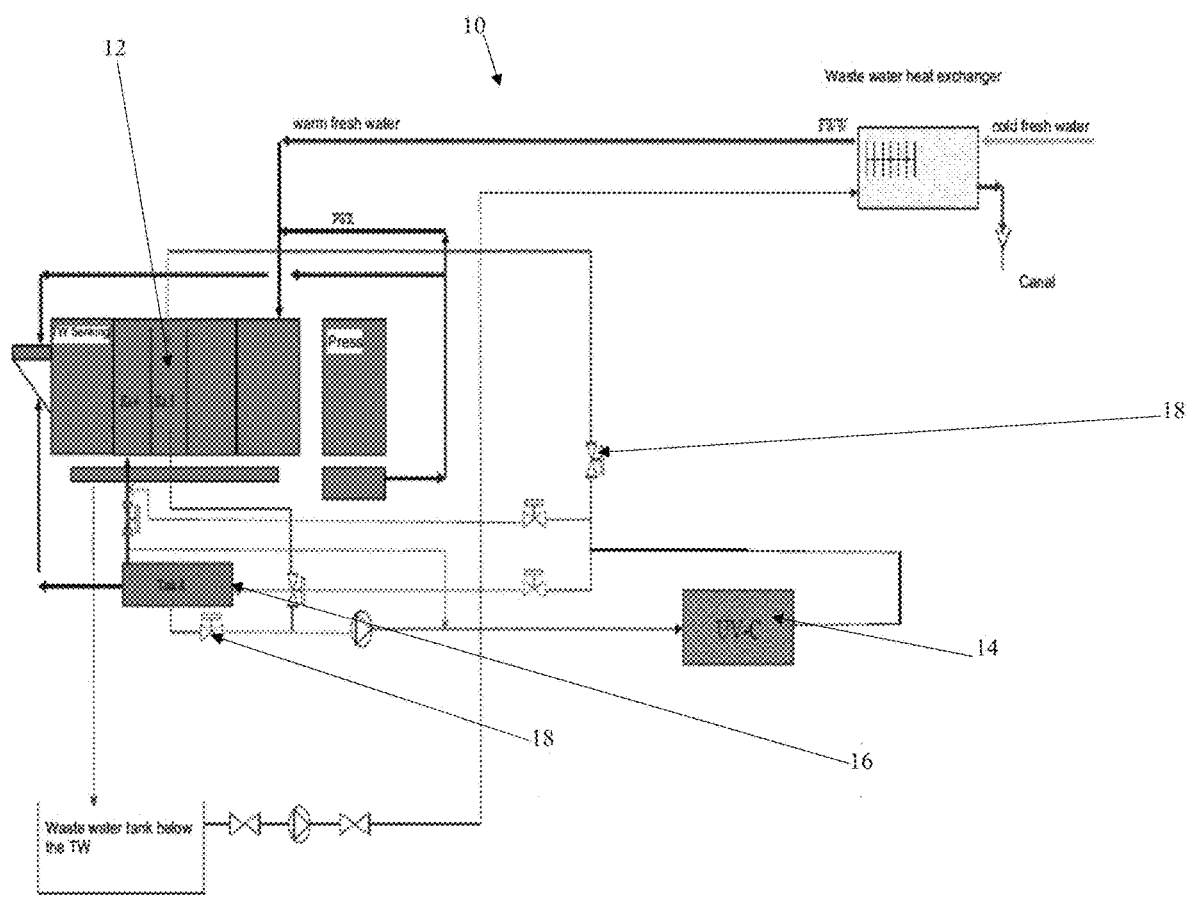

UV-TREATMENT IN INDUSTRIAL LAUNDRY ON INTERMITTENT WASHING SYSTEMS

FIELD OF INVENTION

The present invention relates to a process for laundering textiles in a tunnel washer using UV radiation, a device for performing the process, and the use of UV radiation, especially UVC radiation, in laundering processes for textiles in tunnel washers.

BACKGROUND OF THE INVENTION

In industrial laundering, essentially two different kinds of laundering machines are employed: washing/spin drying machines and tunnel washers. The latter are also referred to as laundry lines or, less frequently, as continuous batch washers (CBW). Washing/spin drying machines are characterized by including only one laundering compartment in the form of a washing drum. As in a conventional household washing machine, the laundry is introduced in the drum, washed therein with a washing liquor, followed by dewatering by spinning. Thus washing/spin drying machines work in a batch mode on principle.

In contrast, tunnel washers enable a continuous operation. The core of a tunnel washer is, for example, a long metallic tube divided into several compartments. The textiles to be washed are introduced into the tunnel washer in the form of individual textile batches on one side of the tube. The textile batches are moved from compartment to compartment at a predetermined pace. In every step, another textile batch can be introduced on the one side of the tube. At the same time, a cleaned textile batch can be removed in every step behind the tube. Thus, the number of textile batches present in the tunnel washer is the same as the number of compartments, and the dwelling time of a textile batch in the tunnel washer corresponds to the number of compartments multiplied the duration of a step. The division of the tunnel washer into compartments can be effected by the plant containing, for example, an Archimedean screw inside. The screw may also cause the transport of the textile batches from compartment to compartment. Other possibilities of transport of the batches include, for example, the so-called dry transfer, or bottom transfer or throw-over system.

Tunnel washers can be divided into four sections in principle:
- 1st section: prewashing
- 2nd section: main washing
- 3rd section: rinsing zone
- 4th section: neutralization and finishing compartment On the side (drain) of the tunnel washer from which the laundered textile batches are removed, fresh water is introduced into the plant and transported in countercurrent of the rinsing zone to the textile batches through the plant. Thus, the textile batches come into contact with the most contaminated water at the beginning of the cleaning process, while the freshest water is employed towards the end of the cleaning process. Washing liquors containing detergents and auxiliary agents can be introduced into the individual compartments of the tunnel washer. No washing liquor should be introduced at least into the last compartment, in order that the textile batch can be cleaned from the detergents and auxiliary agents by means of the fresh water. Downstream of the last compartment, there is usually a dewatering unit, for example, in the form of a press or spin dryer, in which the textile batches are dewatered. The collected water can be treated and reused in the system as a so-called recovery water.

As compared to washing/spin drying machines, tunnel washers are characterized by a continuous operation with a higher capacity, shorter washing time, and improved efficiency. Drawbacks include a higher capital expenditure. A number of possibilities have been proposed to improve the washing performance of industrial washing machines.

Thus, for example, WO 2014/031478 A1 describes a process for cleaning textiles, especially in tunnel washers. The washing liquor contains a detergent and a halogen-containing bleaching agent. The thus treated textiles are subsequently contacted with an aqueous solution containing the peracids. In this way, the cleaning performance is improved.

From WO 2010/144744 A2, a tunnel washer is known that includes a system for the generation of ozone. The ozone can be introduced into one or more of the compartments of the tunnel washer. Ozone has a disinfecting effect.

The use of UV radiation for improving the cleaning performance of washing/spin drying machines is also known in the prior art. Thus, DE 102014 213 312 A1 discloses a washing machine with a bleaching means and a reservoir for water-insoluble particles. From a washing compartment, a washing liquor is directed into a bleaching means, irradiated with UV radiation therein, followed by returning it into the washing compartment. The washing liquor may contain hydrogen peroxide, which is converted to OH free radicals by the UV radiation.

The combination of UV radiation and hydrogen peroxide is also known from EP 1 363 987 B1. A process for cleaning curcuma stains is described therein. Textiles, such as carpets or other fabrics, are exposed to an aqueous hydrogen peroxide solution and irradiated with UV light. In order not to expose the textiles to the damaging action of short-wave UV radiation, long-wave UV radiation in the UVA range is preferably employed.

The tunnel washers known from the prior art have a number of disadvantages. Thus, the use of aggressive chemicals, such as halogen-containing bleaching agents or ozone, results in a burden on the environment. The high temperatures that are typically required are also a burden on the environment. In addition, higher temperatures are accompanied by a higher energy consumption.

Washing methods based on hydrogen peroxide are currently the economically most efficient. However, to date, it has been possible to employ such methods successfully only at washing temperatures above 70° C., because hydrogen peroxide, in particular, exhibits an optimum bleaching and disinfecting action as well as efficient stain removal only from this temperature in the methods known from the prior art. In addition, the use of sodium hypochlorite may be necessary. For this reason, substantially more critical chemicals, such as peracetic acid, peroctanoic acid or pemonanoic acid, are employed in the prior art for washing temperatures below 70° C. Also, ϵ-phthalimido peroxycaproic acid (PAP) is employed at 50° C., neither the cost nor the washing result being economically efficient in this case.

BRIEF SUMMARY OF THE INVENTION

Thus, it is the object of the present invention to provide possibilities for improving the washing performance of tunnel washers, or to limit the use of environmentally harmful chemicals and high temperatures. In particular, a possibility of effectively employing washing methods based on halogen-free washing liquors at temperatures below 70° C. is to be provided.

BRIEF DESCRIPTION OF THE DRAWINGS

The present invention is illustrated and described herein with reference to the various drawings, in which like reference numbers denote like method steps and/or system components, respectively, and in which:

FIG. 1 is a block diagram of the present invention.

DETAILED DESCRIPTION OF THE INVENTION

In a first embodiment, the object of the invention is achieved by a process for laundering textiles with a washing liquor in a tunnel washer 10, which is characterized in that a halogen-free washing liquor is partially or completely irradiated with UV radiation.

According to the invention, the tunnel washer 10 includes two or more compartments 12. The textiles to be washed are transported from compartment 12 to compartment 12 at a predetermined pace. In countercurrent to the textiles, water is directed through the tunnel washer 10. The halogen-free washing liquor, which is irradiated with UV radiation, is fed into one or more compartments 12 of the tunnel washer 10. The method may also include further steps that are known for the laundering of textiles in tunnel washers in the prior art.

"Halogen-free" within the meaning of the present invention excludes the presence of halogen-containing detergents and bleaching agents, for example, sodium hypochlorite.

"UV radiation" as used herein means electromagnetic radiation having a wavelength within a range of from 1 nm to 400 nm, especially from 100 to 400 nm, in accordance with the definition by the World Health Organization (WHO). The spectrum of UV rays is further divided into UVA (315 nm to 380 nm), UVB (280 nm to 315 nm) and UVC radiation (100 nm to 280 nm). The UV spectrum below 100 nm is referred to as extreme UV. Below a wavelength of 0.25 nm, the spectrum of X-rays begins.

The irradiation of the washing liquor with UVC radiation according to the invention decomposes components of the washing liquor to form free radicals. Such free radicals lead to an improved cleaning performance. Consequently, the use of harmful chemicals and the washing temperature can be reduced without a loss of washing performance. The free radicals formed improve the bleaching effect and the ability of the washing liquor to remove stains. The dwelling time in the individual compartments of the tunnel washer 10 can also be reduced. Depending on the mass of the textile batches to be cleaned, step lengths of 80 to 240 seconds can be realized, for example. One textile batch can have a mass of 25 to 100 kg, especially from 35 to 75 kg, for example. In addition, it is possible to exploit the components employed of the washing liquor optimally.

The combination of physical and chemical effects according to the invention forms a very efficient and sustainable washing process with completely new dimensions, also in view of the so-called post washing quotas. Since even persistent stains can now be removed in the first laundering operation, the cost-intensive post washing is now omitted for the most part. The free radicals formed can also have a disinfecting effect. The precursors are commercially available. In this way, the dreaded contamination of the laundry line, which would lead to a very extensive hygienic rehabilitation of the entire machine, can be avoided.

In addition, the process according to the invention has the advantage that it can be performed very easily on the basis of commercially available tunnel washers 10, as shown in FIG. 1. This only requires the integration of a UV reactor 14, with a corresponding liquor control. In this way, the efficiency of existing tunnel washers 10 can be significantly enhanced without a particular expenditure and, in particular, without a high investment cost. Except for the process step of using UV radiation, established washing methods can be essentially employed.

Surprisingly, it has been found that special advantages are obtained from the irradiation of the washing liquor with UV radiation according to the invention in combination with a tunnel washer 10. Thus, the process according to the invention makes use of the fact that the textiles are dwelling in one compartment 12 of the tunnel washer 10 only for a short time anyway. In particular, this dwelling time is clearly shorter as compared to washing/spin drying machines. The free radicals formed by UVC radiation generally have only a short life. While the effect of UV radiation in washing/spin drying machines is only short and thus exists only for part of the washing period, the dwelling time in tunnel washers 10 is so short anyway that the radiation leads to an improved cleaning performance almost for the full washing period. In addition, tunnel washers 10 in combination with UV radiation offer the advantage that washing liquors can be introduced in different compartments 12, and these washing liquors can also be irradiated separately.

The irradiation of the washing liquor according to the invention can be effected immediately in one or more compartments 12 of the tunnel washer 10. In this way, a compartment 12 can be irradiated completely or partially. The formation of free radicals then takes place immediately in the compartment 12 of the tunnel washer 10. This approach offers the particular advantage that the disinfecting effect of the UV radiation acts itself immediately on the textiles.

However, the irradiation of the washing liquor according to the invention may also be effected outside the compartments 12 of the tunnel washer 10 using a separate UV reactor 14 in a bypass flow. For this purpose, washing liquor can be directed from one tank 16 at first through a UV reactor 14, followed by directing irradiated washing liquor into one or more compartments 12 of the tunnel washer 10. The washing liquor may also be irradiated only partially. Washing liquor can be mixed with further non-irradiated washing liquor at any ratio, and such mixture can be fed into one or more compartments 12 of the tunnel washer 10.

It is further possible to supply irradiated washing liquor into a tank 16 and to store it therein for some time. The tank 16 may also be a tank 16 that contains further, non-irradiated washing liquor. Washing liquor may also be directed from one of the compartments 16 of the tunnel washer 10, after it was contacted with textile batches therein, through a UV reactor 14, where it is irradiated. In the following, washing liquor may again be supplied into one of the compartments 12 of the tunnel washer 10, or even stored in a tank 16.

However, the process management is not limited to the variants mentioned.

Preferred embodiments of the process according to the invention are described in the following. The description is exemplary and is not intended to limit the scope of the invention. Other embodiments than those described herein are also possible and included in the invention.

In a preferred embodiment, the washing liquor comprises hydrogen peroxide or peracids in a solvent. Preferably, the solvent is water. Peracids within the meaning of the present invention include, in particular, peracetic acid, peroctanoic acid, pernonanoic acid and ε-phthalimido peroxycaproic acid. Also, mixtures of these with one another and with hydrogen peroxide may be employed according to the invention. The irradiation according to the invention of, for example, the peroxide-containing washing liquor with UVC radiation forms OH free radicals. The OH free radicals formed improve the washing performance of the washing liquor. In addition, the irradiation enables the utilization of the hydrogen peroxide to be improved by reacting unreacted $H_2O_2$ to OH free radicals. This improves the bleaching and disinfecting effect of the peroxide.

The combination according to the invention of a washing liquor based on hydrogen peroxide and irradiation with UVC radiation enables a washing liquor based on hydrogen peroxide to be employed below 70° C. in addition, the addition of sodium hypochlorite can be omitted. The use of critical chemicals, such as peracids, can also be circumvented. Also, when the temperature is reduced to about 45° C., the stain removal is improved, the whiteness increased, and the damage to fibers reduced with the method according to the invention as compared to standard methods at 70° C. without UV irradiation. Optionally, with the washing result being the same as that of the standard methods, the amount of hydrogen peroxide employed can be reduced by 10 to 30%. When the above mentioned peracids are employed, the washing temperature can be reduced drastically.

Preferably, the washing liquor contains further components, such as surfactants, alkali, complexing agents, optical brighteners and bleaching agents. The washing liquor may contain any ingredients usual with washing liquors, without being limited thereto. The ingredients achieve their effects as known from the prior art, but which is surprisingly enhanced further by the UV irradiation according to the invention.

As said surfactants, in particular, non-ionogenic surfactants and/or anionically active surfactants based on fatty alcohol ethoxylates and/or polyglucosides may be employed, without being limited thereto. As said alkali, for example, those based on sodium hydroxide and/or potassium hydroxide may be used, without being limited thereto. As complexing agents, for example, those based on polycarboxylic acid and/or phosphonates as well as sugar acrylic acid polymers and/or comb polymers may be mentioned, without being limited thereto. For example, the washing liquor may contain optical brighteners based on stilbene derivatives, without being limited thereto. Possible halogen-free bleaching agents are those based on hydrogen peroxide, without being limited thereto.

The oxidative UV irradiation clearly enhances the washing power of non-ionogenic surfactants, in particular. Thus, the irradiation of the complete washing liquor with all its components results in a particular increase of washing power. Especially this combination causes a unique washing experience, especially stain removal, under UV influence.

In a preferred embodiment, the washing liquor is irradiated before being supplied to one of the compartments of the tunnel washer. Thus, the irradiation is effected outside the compartments of the tunnel washer. In this way, the textiles have no direct contact with the UV radiation. Consequently, this procedure is characterized by the particular advantage that the textiles cannot be damaged by UV radiation. In addition, the implementation of the process based on commercially obtainable tunnel washers or existing plants is particularly simple, because a UV reactor 14 merely has to be integrated outside the plant into the device for supplying the washing liquor.

The washing liquor to be irradiated before being supplied to a compartment 12 may be derived, for example, from a tank. However, the washing liquor to be irradiated may also be derived from one of the compartments 12. In this way, a washing liquor already supplied to one of the compartments 12 is removed, irradiated outside the chamber, and subsequently supplied to a compartment again.

Preferably, the UV radiation employed includes radiation in the UVC range. More preferably, the UV radiation employed includes radiation within a range of from 250 nm to 270 nm, especially 254 nm. Alternatively, the UV radiation employed may consist exclusively of UVC radiation, preferably of radiation within a range of 254 nm, especially from 250 to 270 nm.

Surprisingly, it has been found that radiation in the UVC range cause a particularly strong activation of the washing liquor. This effect can be still enhanced if the radiation employed exclusively consists of UVC radiation, Thus, for example, the effect of hydrogen peroxide can be enhanced by 4,000 times by UVC radiation. In addition, UVC radiation has the particular advantage that is has a strongly germicidal or bactericidal effect within a wavelength range of about from 250 nm to 270 nm, especially around 258 nm. This property can be explained by the fact that the shortwave high energy UVC radiation stops the maintenance of the metabolism and the cell division by damaging the DNA, so that cells thus damaged will ultimately die. A mutation-dependent resistance formation is excluded. This disinfecting effect decreases with increasing complexity of the attacked organisms. Thus, viruses and bacteria can be destroyed substantially more easily as compared to fungi or fungal spores, for example. However, since UVC rays do not penetrate solid materials on principle, a safe shielding is possible and simple.

Preferably, the laundering of the textiles is performed at a temperature of from 40° C. to 70° C., especially at 50° C. The temperature, which is reduced as compared to those of the methods known from the prior art, reduces the energy consumption and enables a environment-friendly method.

The washing liquor preferably contains hydrogen peroxide and/or peracids in a concentration of 1 to 5, more preferably 1 to 3, especially 1 to 2, g per kg of laundry.

In another embodiment, the object of the invention is achieved by a tunnel washer 10 for performing the above described process. The tunnel washer 10 according to the invention includes two or more compartments 12, a device for the timed transport of textile batches from compartment 12 to compartment 12, a device for supplying water, and a device for supplying a washing liquor to one or more compartments 12, comprising one or more tanks 16 and a transport system, characterized in that said tunnel washer 10 comprises one or more UV reactors 14, The device for supplying water has such a design that the water can be transported in countercurrent to the textile batches through the compartments 12. The UV reactors 14 are either embedded in the transport system for the washing liquor in such a way that the washing liquor can be supplied completely or partially from a tank 16 or one of the compartments 12 of the tunnel washer 10 through one or more UV reactor(s) 14 into the compartments 12 of the tunnel washer 10, or arranged in such a way that the interior space of one or more of the compartments 12 of the tunnel washer 10 can be partially or completely irradiated by UV radiation.

The transport system serves for transporting the washing liquor from a tank 16 into the compartments 12 of the tunnel washer 10. In the alternative in which one or more UV reactors 14 are embedded into the transport system for the washing liquor, the washing liquor can be irradiated outside the compartments 12 of the tunnel washer 10, followed by supplying the irradiated washing liquor to the compartments 12. The transport system can consist of pipelines, flexible tubes or the like. These may be interrupted by valves or the like, so that the flow through the transport system can be controlled.

The transport system may also include pumps that enable liquids to be transported.

The tunnel washer 10 according to the invention is not limited to the components described, but may also comprise other components known in the prior art that are usually incorporated in tunnel washers 10. In the following, preferred embodiments of the tunnel washer 10 according to the invention are described in an exemplary way. The description does not represent a limitation to the invention. Other embodiments are also possible and included in the invention.

In a preferred embodiment of the tunnel washer 10 according to the invention, one or more of the UV reactors 14 are suitable for generating UV radiation, especially in the UVC range. The UV reactors 14 may be suitable for generating UV radiation in a broader wavelength range that includes at least part of the UVC range. The UV reactors 14 may also be suitable for generating exclusively radiation in the UVC range.

The transport system preferably has such a design that the washing liquor irradiated in a UV reactor 14 before being supplied to one of the compartments 12 of the tunnel washer 10 can be returned into the tank 16. In this way, irradiated washing liquor can be stored temporarily and employed at a later time. This preferred embodiment of the device also enables irradiated washing liquor to be mixed with non-irradiated washing liquor in a tank 16. This can be enabled by the fact that a tube, flexible tube or the like leads from a UV reactor 14 back into the tank 16. Preferably, the connection is interrupted by a valve 18.

In another preferred embodiment, the transport system has such a design that the washing liquor irradiated in a UV reactor 14 before being supplied to one of the compartments 12 of the tunnel washer 10 can be mixed with non-irradiated washing liquor from the tank 16, and returned into one or more compartments 12 of the tunnel washer 10, wherein the mixing ratio can be adjusted freely by one or more valves 18.

In this embodiment, a conduit may lead from the tank 16 to the compartments 12 of the tunnel washer 10. Another conduit may lead from the tank 16 to a UV reactor 14. From the UV reactor 14, a conduit may lead away, which may connect to the conduit that leads from the tank 16 to the compartments 12. A valve 18 can be inserted in each of the conduits. The valves 18 can be provided in the conduits leading to the compartments 12 respectively before the connection between the two conduits. A tunnel washer 10 according to the invention with such a design enables the irradiated washing liquor to be dosed exactly.

In an alternative embodiment, the transport system may also have such a design that a conduit leads from one or more compartments 12 to a UV reactor 14, and another conduit leads from this UV reactor 14 back to one or more compartments 12. A tunnel washer 10 according to the invention with such a design is suitable for choosing a process management in which a washing liquor is supplied to a compartment 12 at first, removed from this compartment 12, irradiated outside the compartment 12, and the irradiated liquor is again supplied to the compartment 12. The conduits may contain valves 18 and pumps in order to control or cause the transport of the liquors.

In another embodiment, the object of the invention is achieved by the use of UV radiation in a cleaning process for textiles in a tunnel washer 10. Preferably, the UV radiation has fractions in the UVC range. More preferably, UVC radiation is exclusively used. The radiation may be used to improve the washing power of a washing liquor. Preferably, the UV radiation, especially UVC radiation, is used in combination with a washing liquor containing hydrogen peroxide and/or peracids.

COMPARATIVE EXAMPLE 1

A wash control cloth according to the specifications of RAL-GZ 992/2 "Household and Object Laundry" was tested in a formulation of the prior art on a tunnel washer according to the FIGURE using hydrogen peroxide at 70° C. The wash control cloth was treated for a total of 50 times.

Washing Formulation:
  Prewash: 2 g/kg of laundry of non-ionogenic surfactant
  2 g/kg of laundry of NaOH-based alkali
  Main wash: 2 g/kg of laundry of complexing agent (phosphonate)
  2 g/kg of laundry of NaOH-based alkali
  4 g/kg of laundry of hydrogen peroxide (35%)
  1 g/kg of laundry of optical brightener (stilbene derivative)
  pH neutralization: 3 g/kg of laundry of citric acid
  Results of Standard Formulation

| Testing criteria | | Results | Requirements according to RAL-GZ 992/2 |
|---|---|---|---|
| Strength reduction (loss of tear strength) | | 19.4% | maximum 30% |
| Damage factor (chemical damage) | | 0.3 | maximum 1.0 |
| Ambers (inorganic incrustations) | | 0.1% | maximum 1.0% |
| Whiteness quality | whiteness | 205 | minimum 170 |
| | hue error | −0.48 | R 1.50-G 2.49 |
| | basic whiteness value (Y value) | 88 | minimum 87 |

Example 1

A wash control cloth according to the specifications of RAL-GZ 992/2. "Household and Object Laundry" was tested in the process according to the invention on a tunnel washer according to the FIGURE using hydrogen peroxide at 50° C. and with UVC irradiation of the entire washing liquor. The wash control cloth was treated for a total of 50 times.

Washing Formulation:
  Prewash: 2 g/kg of laundry of non-ionogenic surfactant
  1 g/kg of laundry of NaOH-based alkali
  Main wash: 2 g/kg of laundry of complexing agent (phosphonate)
  1 g/kg of laundry of NaOH-based alkali
  2 g/kg of laundry of hydrogen peroxide (35%)
  1 g/kg of laundry of optical brightener (stilbene derivative)
  pH neutralization: 2 g/kg of laundry of citric acid Results of UVC Formulation

| Testing criteria | | Results | Requirements according to RAL-GZ 992/2 |
|---|---|---|---|
| Strength reduction (loss of tear strength) | | 5.4% | maximum 30% |
| Damage factor (chemical damage) | | 0.1 | maximum 1.0 |
| Ambers (inorganic incrustations) | | 0.1% | maximum 1.0% |
| Whiteness quality | whiteness | 239 | minimum 170 |
| | hue error | N-0.11 | R 1.50-G 2.49 |
| | basic whiteness value (Y value) | 92 | minimum 87 |

The invention claimed is:

1. A process for laundering textiles comprising; providing a tunnel washer with two or more compartments, transporting the textiles from compartment to compartment in a predetermined pace, transporting water through the tunnel washer in counter-current, and supplying a halogen-free washing liquor to one or more compartments, wherein said washing liquor is partially or completely irradiated with UV radiation, characterized in that said washing liquor comprises hydrogen peroxide and/or peracid in a solvent.

2. The process according to claim 1, wherein said peracids include peracetic acid, peroctanoic acid, pernonanoic acid and/or ε-phthalimido peroxycaproic acid including mixtures thereof with one another and with hydrogen peroxide.

3. The process according to claim 1, wherein said washing liquor comprises a solvent and one or more materials selected from the group consisting of surfactants, alkali, complexing agents, optical brighteners and bleaching agents.

4. The process according claim 1, wherein said washing liquor is irradiated with UV radiation before being supplied to one or more compartments of the tunnel washer.

5. The process according to claim 1, wherein the UV radiation employed comprises radiation in the UVC range.

6. The process according to claim 1, wherein the laundering of the textiles is performed at a temperature of from 40 to 60° C.

7. The process according to claim 1, wherein said washing liquor contains hydrogen peroxide at a concentration of from 1 to 5 g/kg of laundry.

8. A tunnel washer comprising two or more compartments, a device for the timed transport of textile batches from compartment to compartment, a device for supplying water, wherein said supplying device has such a design that the water can be transported in counter-current to the textile batches through the compartments, a device for supplying a washing liquor to one or more compartments, comprising one or more tanks and a transport system, wherein said tunnel washer comprises one or more UV reactors, wherein said UV reactors either a) are embedded into the transport system for the washing liquor in such a way that the washing liquor can be conducted wholly or in part from the tank or one of the compartments of the tunnel washer through one or more UV reactors into the compartments of the tunnel washer, or b) are arranged in such a way that the interior space of one or more of the compartments of the tunnel washer can be irradiated partially or completely with UV radiation, characterized in that said UV reactors can produce UV radiation comprising radiation in the UVC range.

9. The tunnel washer according to claim 8, wherein the washing liquor is irradiated in a UV reactor before being supplied to one of the compartments of said tunnel washer.

10. The tunnel washer according to claim 8, wherein the washing liquor is irradiated in a UV reactor before being supplied to one of the compartments of said tunnel washer and can be mixed with a non-irradiated washing liquor from the tank and supplied to one or more compartments of said tunnel washer, wherein the mixing ratio can be adjusted freely by one or more valves.

* * * * *